(12) United States Patent
Hurson

(10) Patent No.: US 8,272,871 B2
(45) Date of Patent: *Sep. 25, 2012

(54) TRANSFER COPING FOR DENTAL IMPLANTS

(75) Inventor: Steven M. Hurson, Yorba Linda, CA (US)

(73) Assignee: Nobel Biocare Service AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/377,259

(22) Filed: Mar. 16, 2006

(65) Prior Publication Data

US 2006/0228672 A1    Oct. 12, 2006

Related U.S. Application Data

(60) Provisional application No. 60/662,950, filed on Mar. 17, 2005, provisional application No. 60/678,095, filed on May 5, 2005.

(51) Int. Cl.
*A61C 8/00* (2006.01)
(52) U.S. Cl. ...................................................... 433/173
(58) Field of Classification Search ............ 433/172–176
See application file for complete search history.

(56) References Cited

U.S. PATENT DOCUMENTS

| | | | |
|---|---|---|---|
| 4,290,755 A | 9/1981 | Scott | |
| 4,854,872 A | 8/1989 | Detsch | |
| 4,856,994 A | 8/1989 | Lazzara et al. | |
| 5,108,288 A | 4/1992 | Perry | |
| 5,125,839 A | 6/1992 | Ingber et al. | |
| 5,195,891 A | 3/1993 | Sulc | |
| 5,213,500 A | 5/1993 | Salazar et al. | |
| 5,238,405 A | 8/1993 | Marlin | |
| 5,302,126 A | 4/1994 | Wimmer et al. | |
| 5,334,024 A | 8/1994 | Niznick | |
| 5,417,570 A | 5/1995 | Zuest et al. | |
| 5,431,567 A | 7/1995 | Daftary | |
| 5,527,182 A | 6/1996 | Willoughby | |
| 5,527,183 A | 6/1996 | O'Brien | |
| 5,556,280 A | 9/1996 | Pelak | |
| 5,564,924 A * | 10/1996 | Kwan | 433/173 |
| 5,569,037 A | 10/1996 | Moy et al. | |
| 5,636,989 A * | 6/1997 | Somborac et al. | 433/173 |
| 5,662,476 A | 9/1997 | Ingber et al. | |
| 5,688,123 A | 11/1997 | Meiers et al. | |

(Continued)

FOREIGN PATENT DOCUMENTS

JP    2000-512884    10/2000

(Continued)

OTHER PUBLICATIONS

Branemark System, 1995 brochure, Nobelpharma USA, Inc.

(Continued)

*Primary Examiner* — Sunil K Singh
(74) *Attorney, Agent, or Firm* — Knobbe Martens Olson & Bear, LLP

(57) ABSTRACT

A dental implant component includes a distal end that includes a top surface and a proximal end that defines an opening. An inner surface of the component defines an internal cavity. At least one resiliently deflectable prong is disposed in the internal cavity. The prong is configured to releasingly engage a groove formed in a bore of a prosthetic abutment. The component further comprising elongated protrusions positioned within the inner surface configured to engage grooves formed in an inner bore of the abutment.

12 Claims, 8 Drawing Sheets

U.S. PATENT DOCUMENTS

| | | | |
|---|---|---|---|
| 5,755,574 A | 5/1998 | D'Alise | |
| 5,904,483 A | 5/1999 | Wade | |
| 6,227,856 B1 * | 5/2001 | Beaty et al. | 433/172 |
| 6,312,260 B1 * | 11/2001 | Kumar et al. | 433/174 |
| 6,332,777 B1 | 12/2001 | Sutter | |
| 6,431,867 B1 | 8/2002 | Gittelson et al. | |
| 6,527,554 B2 * | 3/2003 | Hurson et al. | 433/173 |
| 6,726,480 B1 * | 4/2004 | Sutter | 433/173 |
| 6,769,913 B2 * | 8/2004 | Hurson | 433/173 |

FOREIGN PATENT DOCUMENTS

| | | |
|---|---|---|
| UK | 2119258 | 11/1983 |
| WO | WO 98/32393 A1 | 7/1998 |
| WO | WO 99/17676 A2 | 4/1999 |
| WO | WO 99/17676 A3 | 4/1999 |
| WO | WO 03/051224 A2 | 6/2003 |
| WO | WO 03/051224 A3 | 6/2003 |
| WO | WO 03051224 A2 * | 6/2003 |
| WO | WO 2006/101957 | 9/2006 |

OTHER PUBLICATIONS

The Emergence Profile System, 3i Implant Innovations, 1993.
DENTSPLY Implant advertisement, 1995.
*International Search Report and the Written Opinion of the International Searching Authority*, mailed Jul. 17, 2006 in corresponding International Application No. PCT/US2006/009480, 13 pp.
International Preliminary Report on Patentability and the Written Opinion of the International Search Authority, Issued Sep. 18, 2007 in corresponding International Application No. PCT/US2006/009480, in 8 pages.

\* cited by examiner

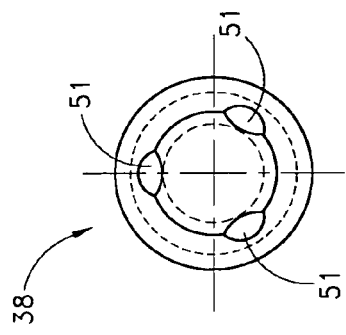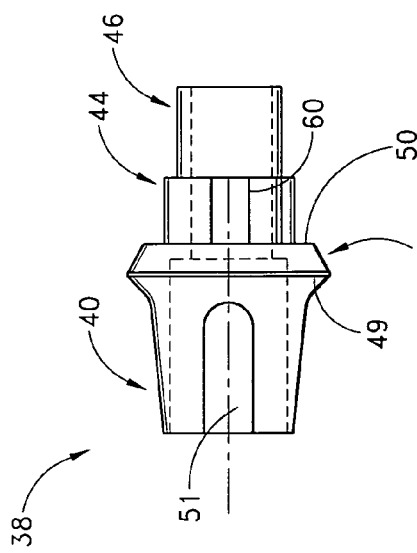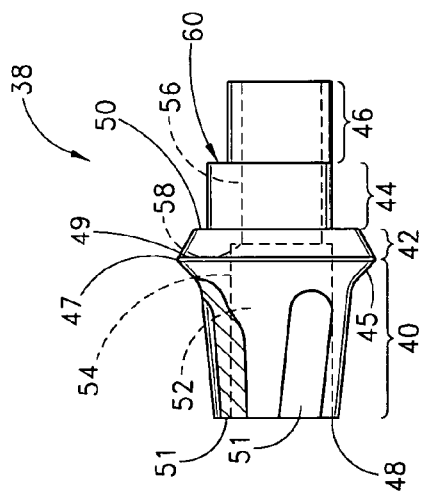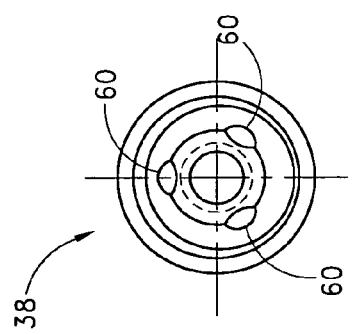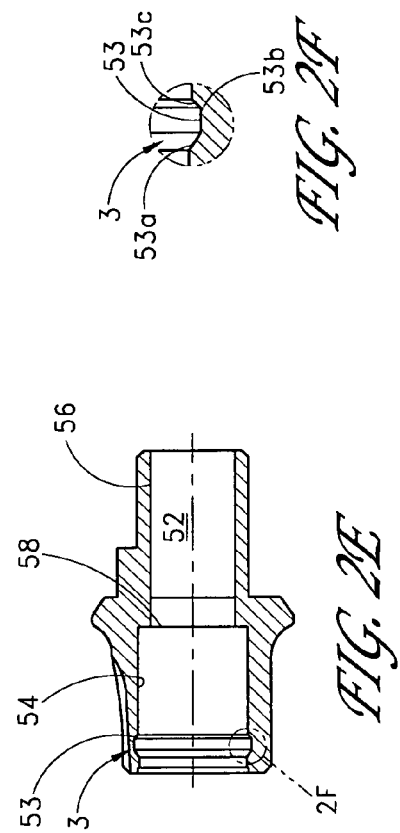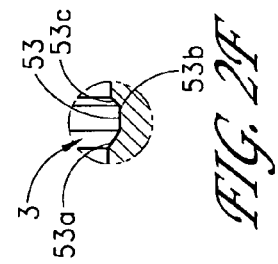

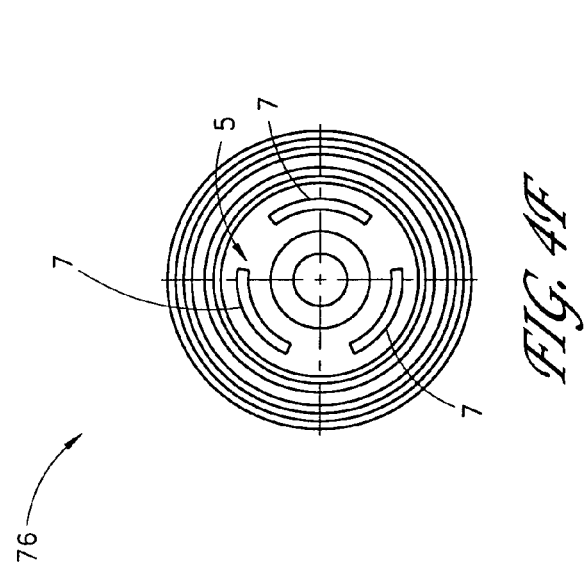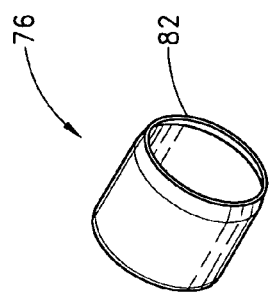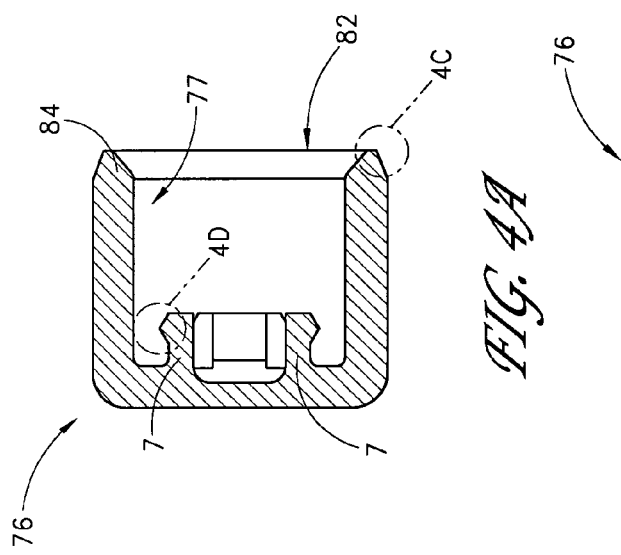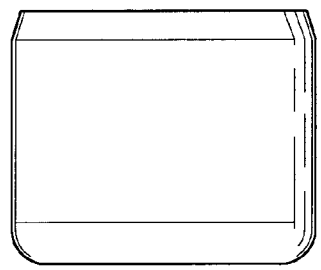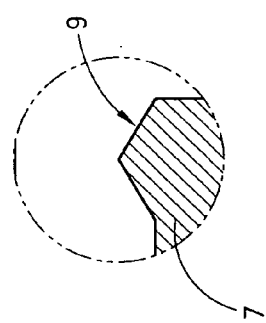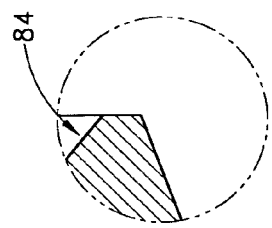
FIG. 4F
FIG. 4E
FIG. 4A
FIG. 4B
FIG. 4D
FIG. 4C

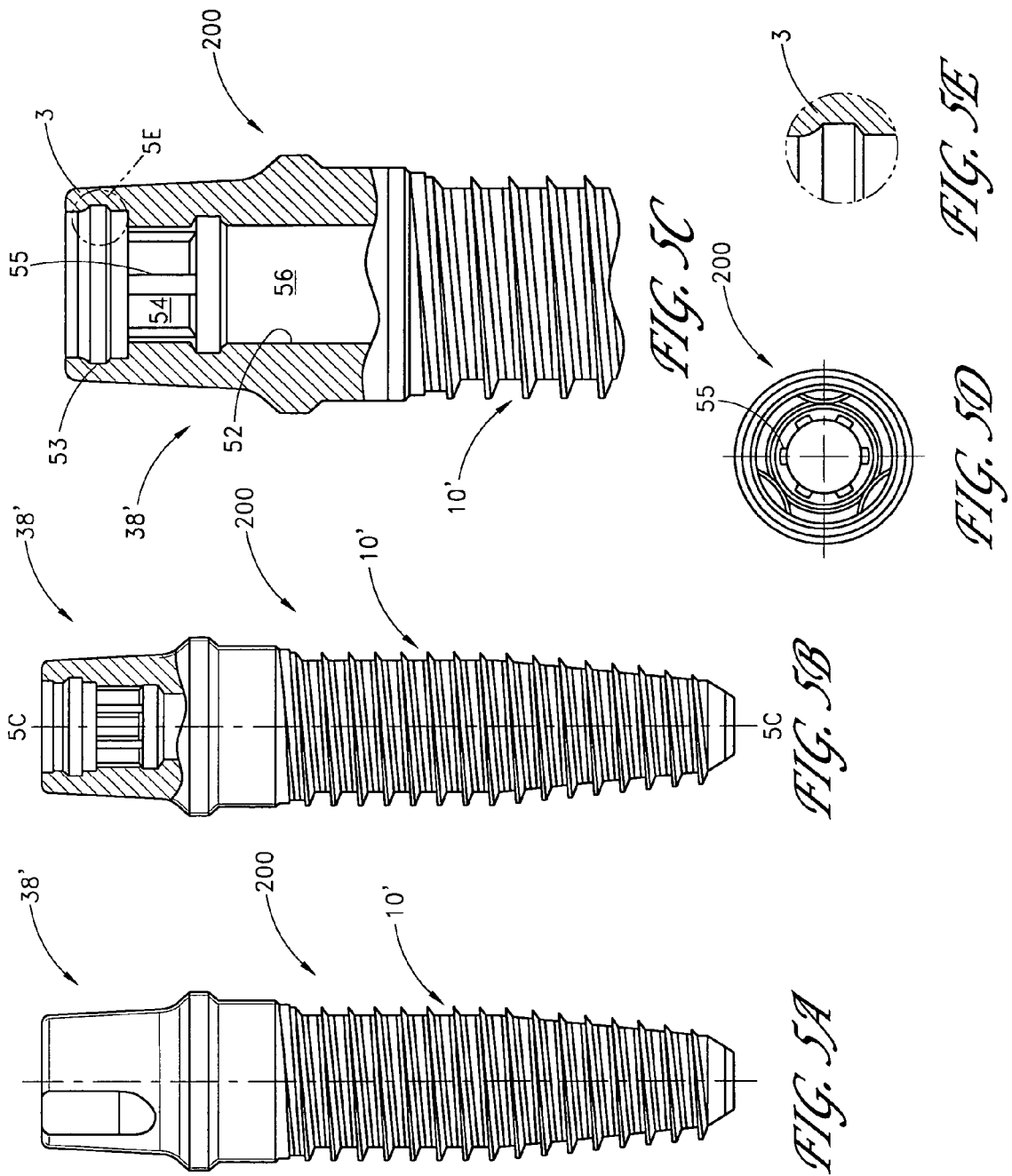

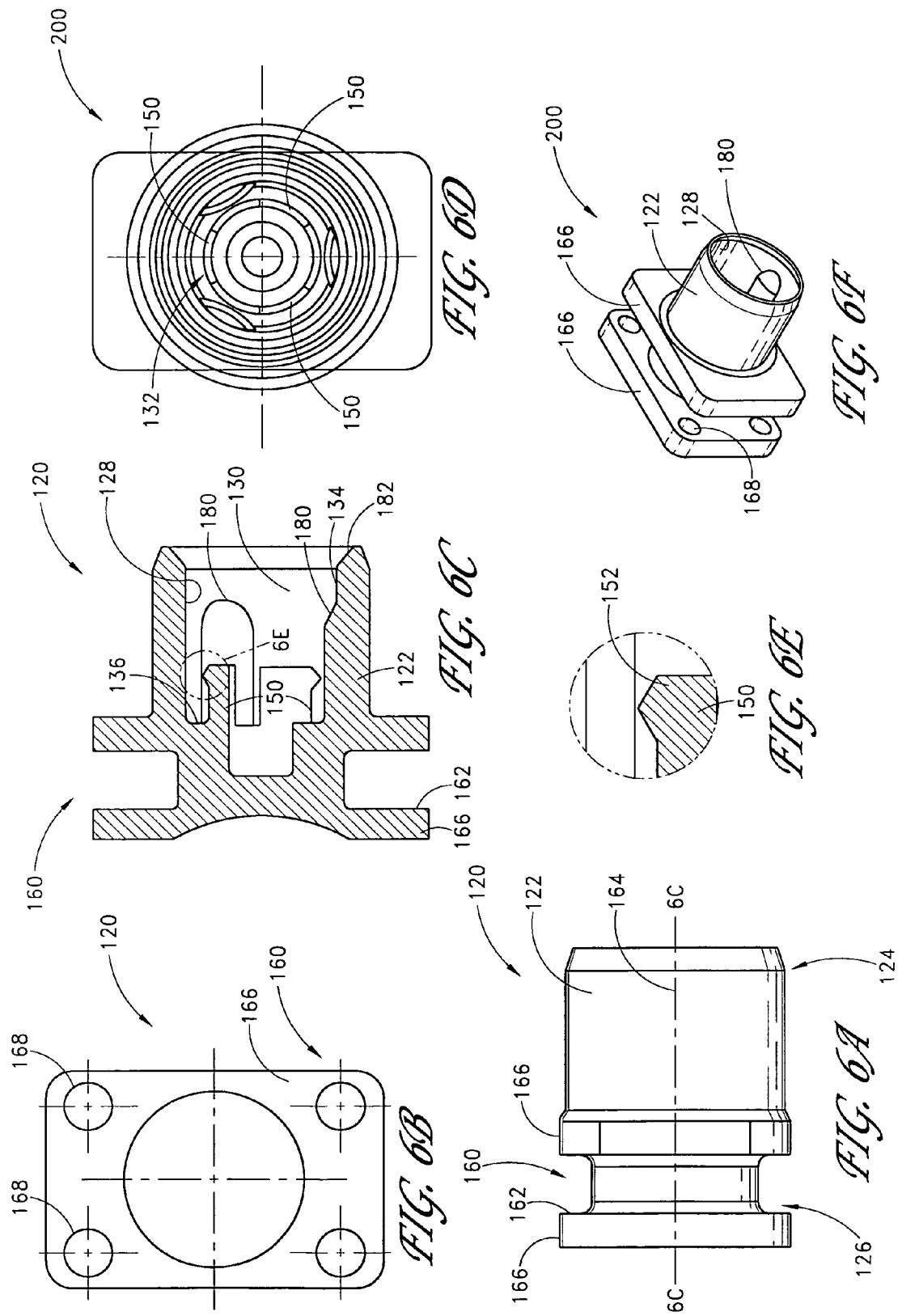

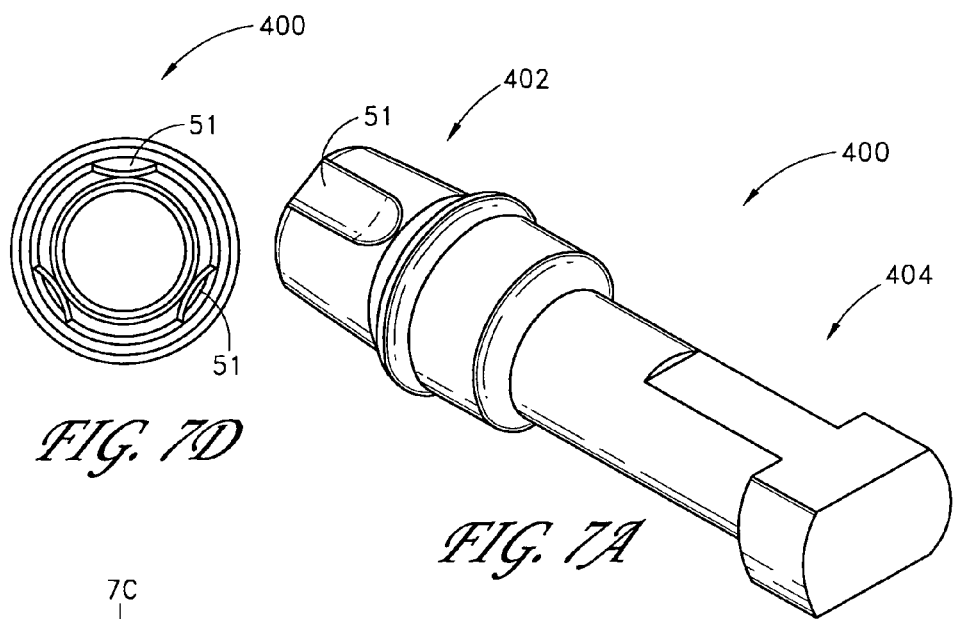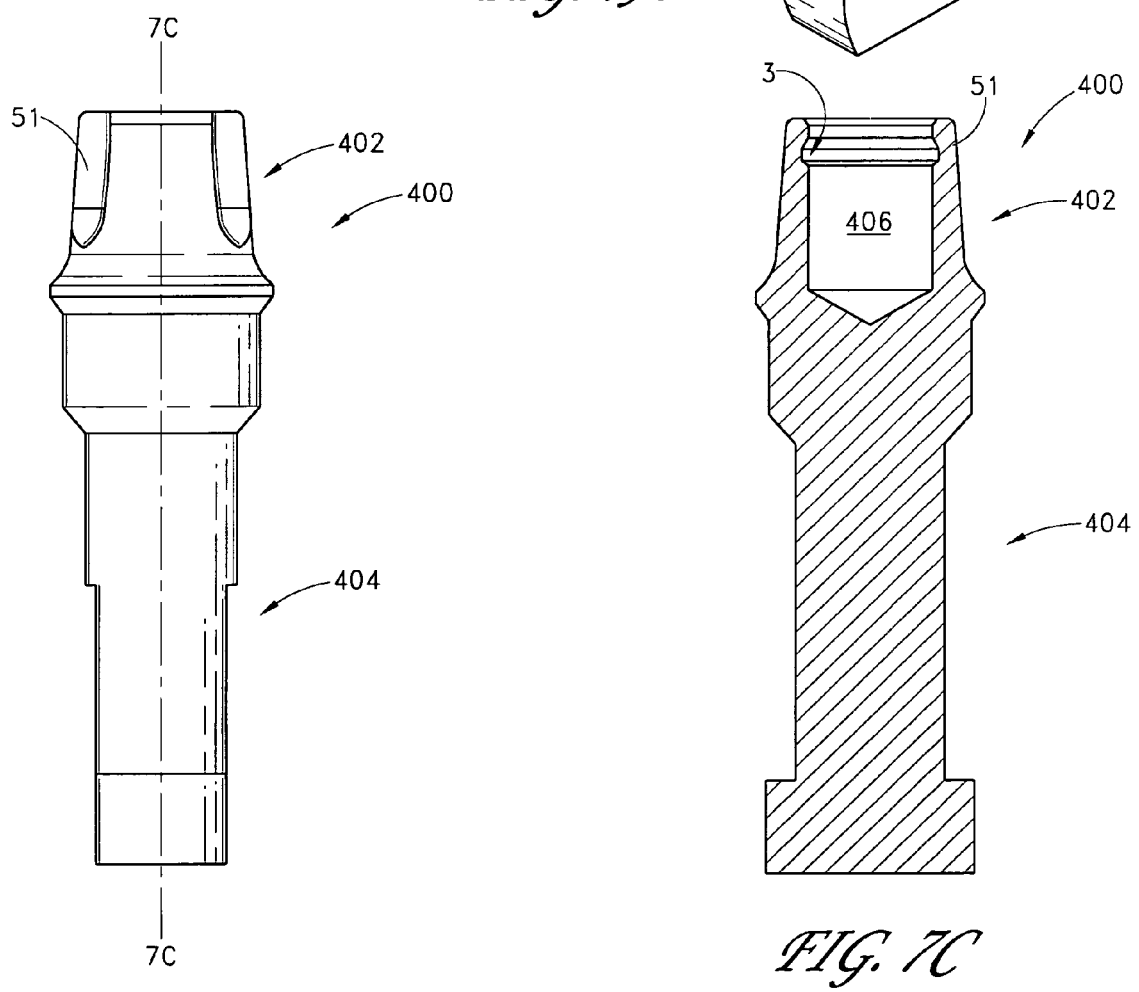

TRANSFER COPING FOR DENTAL IMPLANTS

CROSS-REFERENCE TO RELATED APPLICATIONS

This application claims the benefit of U.S. Provisional Patent Application No. 60/662,950, filed Mar. 17, 2005, the entire contents of which are hereby incorporated by reference herein. This application also claims the benefit of U.S. Provisional Patent Application No. 60/678,095, filed May 5, 2005, the entire contents of which are hereby incorporated by reference herein

BACKGROUND OF THE INVENTION

1. Field of the Invention

The present invention relates generally to dental implants and, more particularly, methods and devices for installing a dental implant.

2. Description of the Related Art

Restoration of an edentulous area of the mouth serves multiple functions, including improved aesthetics, improved mastication, maintenance of crestal bone, and providing for an occlusal stop for a reproducible bite. Restoration can be accomplished using a standard bridge, a removable appliance (a partial or full denture), or a dental implant.

Dental implantation is a procedure for replacing a missing tooth using a dental implant. The placement of the implant is usually accomplished in four stages. In a first stage, a dentist reviews radiographs and dental models to determine the proper placement and axial alignment of the implant. In a second stage, a dental surgeon accesses the bone through the mucosal tissue. With the use of a prefabricated stint, the surgeon drills or bores out the maxillary or mandibular bone. The implant is then either pressed or screwed into the bone. A healing cap is typically then placed over the implant and the surrounding mucosal tissues are sutured over the healing cap. This provides for a biologically closed system to allow osteointegration of bone with the implant. Complete osteointegration typically takes anywhere from four to ten months.

Stage three, involves a second surgical procedure during which the dental surgeon makes an incision in the mucosal tissue to expose the osteointegrated implant. The healing cap is removed and a temporary abutment, having a height at least equal to the thickness of the gingival tissue or a final prosthetic abutment, is coupled to the implant. Once the abutment is secured an immediate mold or impression may be taken. In a modified procedure, the impression may be taken within one to two weeks after stage three. The impression is used to record the axial position and orientation of the implant, which is then reproduced in a stone or plaster analogue of the patient's mouth. The main objective of the impression is to properly transfer the size and shape of adjacent teeth in relation to the permanently placed implant and the precise configuration and orientation of the abutment to the dental technician. The plaster analogue provides the laboratory technician with a precise model of the patient's mouth, including the orientation of the implant fixture relative to the surrounding teeth. Based on this model, the technician constructs a final restoration. Stage four, in the restorative process, involves replacing the temporary healing abutment with the final restoration.

As noted above, during stage three, a mold or impression is taken of the patient's mouth to accurately record the position and orientation of the implant site and to provide the information needed to fabricate the restorative replacement and/or intermediate prosthetic components. There are several conventional methods for taking this impression.

One method involves a conventional transfer coping. Transfer copings have an impression portion adapted to form a unique or indexed impression in the impression material and a base portion having mating indexing means adapted to mate with the exposed indexing means of the implant or prosthetic abutment. In use, the transfer coping is temporarily secured to the exposed proximal end of the implant fixture such that the mating indexing means of the impression coping and implant are interlockingly mated to one another. Typically, a threaded screw or bolt is used to temporarily secure the transfer coping to the implant fixture.

Once the impression coping is secured to the implant fixture, an impression of the transfer coping relative to the surrounding teeth is taken. Typically, this involves a "U" shaped tray filled with an impression material that is placed in the patient's mouth over the implant site. The patient bites down on the tray, squeezing the impression material into the implant site and around the transfer coping. Within a few minutes, the impression material cures or hardens to a flexible, resilient consistency. The impression tray is then removed from the patient's mouth to reveal an impression of the implant site and the transfer coping. The restorative dentist then removes the transfer coping from the patient's mouth and transfers the transfer coping back into the impression material, being careful to preserve the proper orientation of the indexing means.

Another method typically involves a conventional pick-up coping. Pick-up copings are similar to the transfer copings described above; except that a pick-up coping typically includes an embedment portion adapted to be non-removably embedded within the impression material. Typically, the embedded portion comprises a protuberant "lip" or similar embedment projection at a coronal portion of the coping. This allows for "grabbing" or traction of the impression material as the tray is being removed from the patient's mouth. The pick-up copings are "picked up" and remain in the impression material when the tray is removed from the patient's mouth.

Yet another method for taking an impression involves an impression or transfer cap. Impression or transfer caps are placed over or on the built-up part of the abutment or the implant and remain in the impression material when the tray is removed. There are several different types of transfer caps. One type of transfer cap has a tapered inner surface, which is adapted in form and size to the built-up part or abutment of the implant. This cap has an inner surface, which has indentations or slots, which correspond to indentation or slots present on the abutment. The cap is attached to the abutment with resilient flaps or tongues. An example of such a cap is illustrated in U.S. Pat. No. 5,688,123 to Meiers et al.

SUMMARY OF THE INVENTION

A disadvantage of the type of cap described in Meiers et al. is that the cap attaches to the abutment of the implant via the flaps, which extend over the shoulders of a conical area of the abutment. Because the shoulders of the abutment are next to the gum line, it is difficult to position the flaps over the shoulders. Moreover, the location of the shoulders next to the gum line may result in the incomplete seating of the transfer cap on the shoulders, causing the transfer cap to disengage from the abutment before the impression is taken. Additionally, because the patient's gum line may be sensitive due to the insertion of the implant, contact between the transfer cap and the gum line can produce discomfort or pain in the patient. Therefore, there is a need for an improved transfer cap.

In accordance with one embodiment of the invention, a dental implant component includes a distal end that includes a top surface and a proximal end that defines an opening. An inner surface of the component defines an internal cavity. At least one resiliently deflectable prong is disposed in the internal cavity. The prong is configured to releasingly engage a groove formed in a bore of a prosthetic abutment. The component further comprising elongated protrusions positioned within the inner surface configured to engage grooves formed on an outer surface of the abutment.

In accordance with another embodiment of the invention, a dental implant system, comprises a dental implant, an abutment and a mating component. The abutment comprises an upper region and an inner bore having an engagement feature positioned therein. The mating component has proximal end that defines an opening and an inner surface that defines an internal cavity for receiving the upper region of the abutment. A complementary engagement feature is disposed in the internal cavity and is configure to releaseably engage the engagement feature within the inner bore.

Another embodiment of the present invention comprises a method of coupling a dental component to an abutment of a dental implant system. A dental component having an internal cavity is positioned over an upper portion of an abutment. And the dental component is pressed onto the abutment until an engagement feature within the internal cavity of the abutment engages a complementary engagement feature within a bore of the abutment.

BRIEF DESCRIPTION OF THE DRAWINGS

These and other features of the invention will now be described with reference to the drawings of the preferred embodiments, which are intended to illustrate and not to limit the invention, and in which:

FIG. 2A is a side view of one embodiment of a abutment, which is configured to mate with the embodiment of the dental implant of FIG. 1A or FIG. 1D;

FIG. 2B is another side view of the abutment of FIG. 2A;

FIG. 2C is a top plan view of the abutment of FIG. 2A;

FIG. 2D is a bottom plan view of the abutment of FIG. 2A;

FIG. 2E is a cross-sectional side view of the abutment of FIG. 2A;

FIG. 2F is a enlarged view of the portion labeled 2F in FIG. 2E;

FIG. 4A is a cross-sectional view of one embodiment of a healing cap;

FIG. 4B is a side plan view of the healing cap of FIG. 4A;

FIG. 4C is a close up view of a portion of FIG. 4A labeled 4C;

FIG. 4D is a close up view of a portion of FIG. 4A labeled 4D;

FIG. 4E is a rear perspective view of the healing cap of FIG. 4A;

FIG. 4F is a top plan view of the healing cap of FIG. 4A;

FIG. 5A is a side view of one embodiment of a dental implant;

FIG. 5B is a side view of the dental implant of FIG. 5A with a top portion shown in cross-section;

FIG. 5C is an enlarged view of the top portion of FIG. 5B;

FIG. 5D is a top view of the dental implant of FIG. 5A;

FIG. 5E is an enlarged view of the portion of FIG. 5C labeled 5E;

FIG. 6A is a side view of an impression cap;

FIG. 6B is a top plan view of the impression cap of FIG. 6A;

FIG. 6C is a cross-sectional side view of the impression cap of FIG. 6A;

FIG. 6D is a bottom plan view of the impression cap of FIG. 6A;

FIG. 6E is a close up view of a portion of FIG. 6C labeled 6E; and

FIG. 6F is rear perspective view of the impression cap of FIG. 6A;

FIG. 7A is side perspective view of an analogue of an abutment;

FIG. 7B is a side view of the analogue of FIG. 7A;

FIG. 7C is a cross-sectional side view taken through line 7C-7C of FIG. 7B;

FIG. 7D is a top plan view of the analogue of FIG. 7A;

DETAILED DESCRIPTION OF THE PREFERRED EMBODIMENTS

Figure 1A:
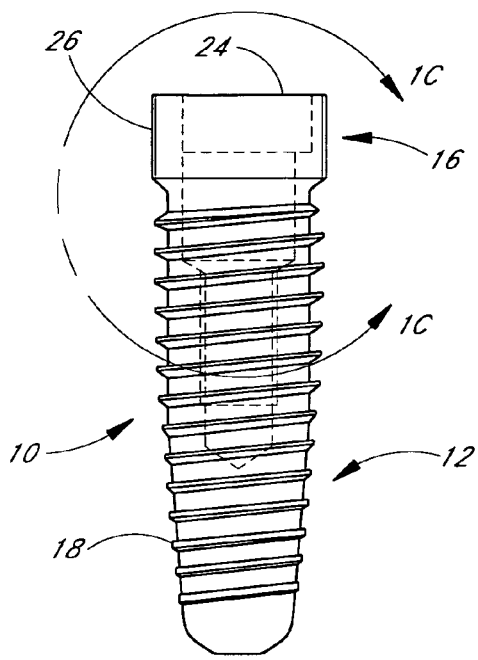
FIG. 1A is a side view of one embodiment of a dental implant.
Figure 1B:
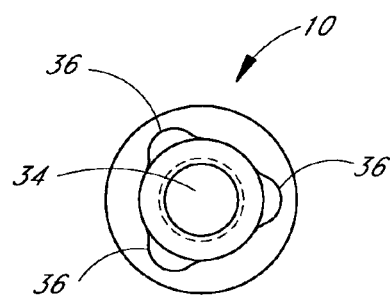
FIG. 1B is a top plan view of part of the dental implant of FIG. 1A.
Figure 1C:
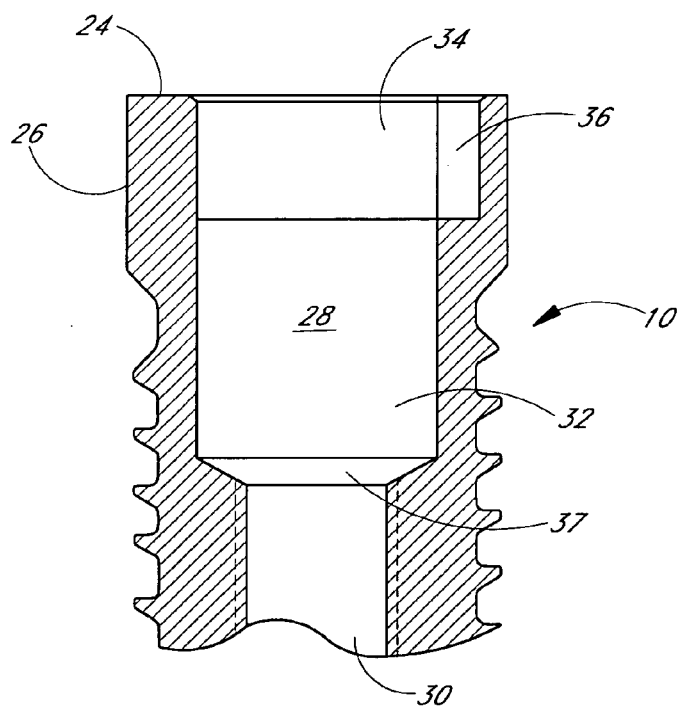
FIG. 1C is a cross-sectional view of the dental implant of FIG. 1A.

The embodiments described herein relate to methods and devices that relate to protecting and/or taking an impression of an abutment, which is coupled or formed with a dental implant. FIGS. 1A-1C illustrate one exemplary embodiment of a dental implant 10, which will be used to illustrate certain features and aspects of the present invention. The dental implant 10 is described in detail in co-pending U.S. application Ser. No. 09/670,708, filed Sep. 27, 2000, the disclosure of which is hereby incorporated herein by reference.

Figure 1D:
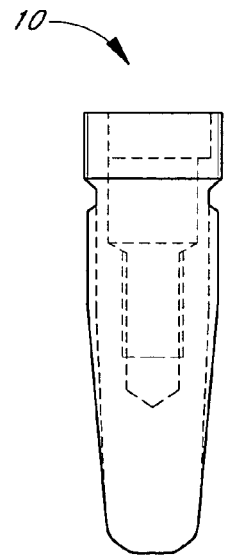
FIG. 1D is a side view of a modified embodiment of a dental implant.

As best seen in FIG. 1A, the implant 10 includes a body portion 12 and a collar 16. The body portion 12 is preferably tapered and includes threads 18 that mate to a preformed threaded hole or osteotomy formed in the patient's jawbone (not shown). However, it should be appreciated that the body portion 12 can also be configured so as to be self-tapping. It should also be appreciated that although the illustrated body portion 12 is tapered or conical, the body portion 12 can be substantially cylindrical. Moreover, in a modified embodiment, the body portion 12 can be unthreaded, as shown in FIG. 1D, if the surgeon prefers to use an unthreaded implant 10. The implant 10 is preferably made of a dental grade titanium alloy, although other suitable materials can also be used.

The collar 16 of the illustrated implant 10 is substantially cylindrical and has a top surface 24 that is substantially flat. The collar 16 is defined in part by a vertical side wall 26 that in one embodiment is approximately 2 millimeters in axial length. In modified embodiments, the collar 16 may have a conical or tapered side wall and/or a top surface that 24 is saddle-shaped or sloped.

As best seen in FIG. 1C, the implant 10 also includes an internal socket 28. The internal socket 28 preferably includes a threaded chamber 30, a post receiving chamber 32, and an anti-rotation chamber 34.

With reference to FIGS. 1B and 1C, the anti-rotation chamber 34 has a central portion having a substantially cylindrical shape. The anti-rotation chamber 34 further includes one or more radially extending rotational engagement portions each comprising a channel or lobe 36 extending from the top surface 24 to the bottom of the indexing chamber 34. In the illustrated implant, three engagement portions 36 are provided, each having a substantially half circular shape. As best seen in FIG. 1B, the engagement portions 36 are situated and evenly spaced around the perimeter of the anti-rotation chamber 34. Each engagement portion 36 may be spaced 120 degrees apart from each other. The anti-rotation chamber 34 is designed to mate with a corresponding anti-rotation region formed on various mating components, such as, for example, a final abutment. The anti-rotation chamber 34 primarily serves to prevent relative rotation between the mating component and the implant 10.

It should be appreciated that in some embodiments the implant 10 does not include the anti-rotation chamber 34. However, the implant 10 preferably includes the anti-rotation chamber 34 because it helps to prevent the relative rotation between the mating components (e.g., a final abutment) and the implant 10. It should also be appreciated that the anti-rotation chamber 36 can be formed into a wide variety of other suitable shapes that may be used with efficacy, giving due consideration to the goals of providing anti-rotation of mating components. For example, the anti-rotation chamber 36 could comprise a hexagonal recess or protrusion that is situated on the top surface 24 of the implant 10. Nevertheless, the illustrated embodiment is preferred because it provides optimal clinical efficacy, ease of use and also minimizes stress concentrations within the anti-rotation chamber 34.

The post-receiving chamber 32 lies between the anti-rotation chamber 34 and the threaded chamber 30. The post-receiving chamber 32 may have a diameter that is less than the diameter of the anti-rotation chamber 36. The post-receiving receiving chamber 32 may include a chamfered region 37, which is adjacent the threaded region 30. As will be explained below, the post-receiving chamber 32 is sized and dimensioned to receive a post that is attached to a mating dental component. The post and the post-receiving chamber 32 provide lateral support, which prevents the mating component from tipping off the implant. However, it should be appreciated that in some embodiments the implant 10 can be formed without the post-receiving chamber 32.

The threaded chamber 30 lies below the post-receiving chamber 32. The threaded chamber 30 is threaded and has a diameter that may be less than the post-receiving chamber 32.

FIGS. 2A-2F illustrate an embodiment of an abutment 38 having certain features and advantages according to an embodiment of present invention. The illustrated abutment 38 is sized and dimensioned to mate with the implant 10 described above. As with the dental implant 10, the abutment 38 is preferably made of a dental grade titanium alloy, although other suitable materials can be used. In another preferred embodiment, the implant 10 and abutment 38 are formed as a unitary structure, as further discussed below.

As best seen in FIG. 2A, the outer surface of final abutment 38 preferably includes an upper region 40, a flared region 42, an anti-rotation region 44, and a post 46. In the preferred embodiment, the upper region 40 is substantially smooth and tapered. The upper region 40 also has a top surface 48 that is substantially flat. Towards the bottom of the upper region (i.e., the portion nearest the flared region 42) is a flared portion 45 that flares outward towards a shoulder or ridge 47. The flared region 42 extends from the shoulder 47 and connects the upper region 40 to a bottom surface 50, which preferably is substantially flat. A margin 49 (see FIG. 2B) defines an interface between the shoulder 47 and the flared portion 45.

The upper region 40 also preferably includes a plurality of grooves 51. These grooves 51 help orient and prevent the rotation of mating component (not shown), such as, for example, a final restoration, which typically has an inner surface that matches or engages the shape of the upper region 40 of the abutment 38. Of course, those skilled in the art will readily appreciate that the upper region 40 and the grooves 51 can be formed into a variety of other shapes that can also provide an anti-rotational interface between the mating component and the abutment 38.

It should be appreciated that although the illustrated cross-sections of the upper region 40 and flared region 42 are round in modified arrangements the cross-sections can be non-round. For example, the cross-section of the upper region and flared region can have a non-round cross-section that resembles the cross-section of a natural tooth. In addition, the shoulder 47 need not be horizontal as it is shown in the illustrated embodiment. For example, in modified embodiments, the shoulder can be sloped, saddle shaped etc.

To permanently secure a final restoration, cement can be applied to the upper region 40 of the abutment 38. Alternatively, the final restoration can be coupled to the abutment 38 by a screw (not shown). In such an arrangement, a screw hole (not shown) can be provided on the side of the abutment 38.

As shown in FIG. 2E, the abutment 38 advantageously includes an inner bore 52 that extends through the center of the abutment 38. The inner bore 52 is preferably defined by a first and second region 54, 56. The diameter of the first region 54 is preferably slightly larger than the diameter of the second region 56. Accordingly, a seat 58 is formed between the first and second regions 54, 56. The seat 58 supports a coupling screw 62 (see FIG. 3A), which will be described in detail below. Optionally, the second region 56 can include internal capture threads (not shown).

With continued reference to FIG. 2E, the abutment 38 includes an engagement feature 3, which is configured to engage complementary engagement figure of another component. As will be explained in more detail below, the engagement feature 3 and complementary engagement feature can be configured to provide an interference fit, a friction fit, or a snap-fit between the two components. In the preferred embodiment, a snap fit is formed between the two components. As shown in FIG. 2F, the engagement feature comprises a circumferentially extending groove 53 formed on the surface of the first region 54 of the inner bore 52. Preferably, the groove 53 has a trapezoidal cross-section, with one surface 53a of the groove 53 extending at a different angle relative to a base 53b of the groove 53 than a second surface 53c. In modified embodiments, the groove 54 can be circular, smooth, rectangular, etc. In still other embodiments, the engagement feature 3 can be configured in a different manner to mate with the engagement feature of the other component. For example, the engagement feature may comprise an annular protrusion or series of protrusions, prongs and the like that engage corresponding recesses and/or prongs on the other component.

With reference back to FIG. 2A, the diameter of the bottom surface 50 is preferably approximately equal to the diameter of the top surface 24 of the implant 10. Extending from the bottom surface 50 is the anti-rotation region 44, which is sized and dimensioned to fit within the anti-rotation chamber 36 of the implant. Accordingly, as best seen in FIGS. 2B and 2D, the anti-rotation region 44 is substantially cylindrical and includes three protrusions 60. The protrusions 60 preferably extend along the entire length of the anti-rotation region 44 and have a half circular shape. The protrusions 60 are arranged around the perimeter of the indexing region 44 approximately 120 degrees apart relative to the center axis of the final abutment 38.

As with the anti-rotation chamber 36 of the implant 10, it should be appreciated that the abutment 38 can be configured without the anti-rotation region 44. However, it is preferred that the abutment 38 include the anti-rotation 44 because it helps to prevent relative rotation between the implant 10 and the final abutment 38. It should also be appreciated that the anti-rotation region 44 can be formed into a wide variety of other suitable shapes that may be used with efficacy to prevent rotation of the implant 10 and the final abutment 38.

Below the indexing region 44 is the post 46. The post 46 is substantially cylindrical and is sized and dimensioned to fit within the post-receiving chamber 32 of the implant 10. As mentioned above, the post 36 provides lateral support to the abutment 38 when it is placed upon the implant 10. However, it should be appreciated in a modified embodiment the abutment 38 can be configured without the post 46.

Figure 3A:
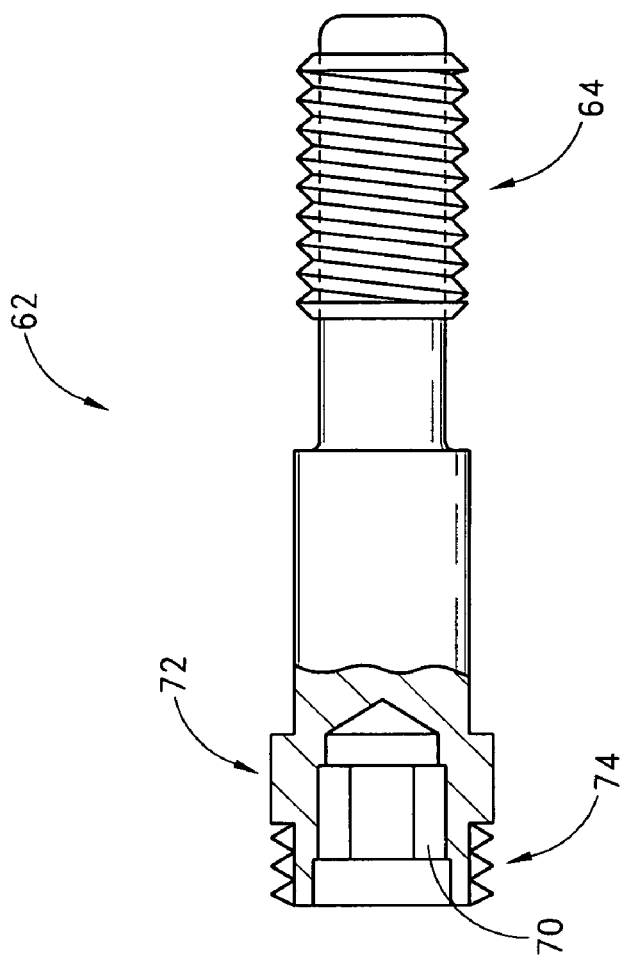
FIG. 3A is a partial cross-sectional side view of one embodiment of a coupling screw.
Figure 3B:
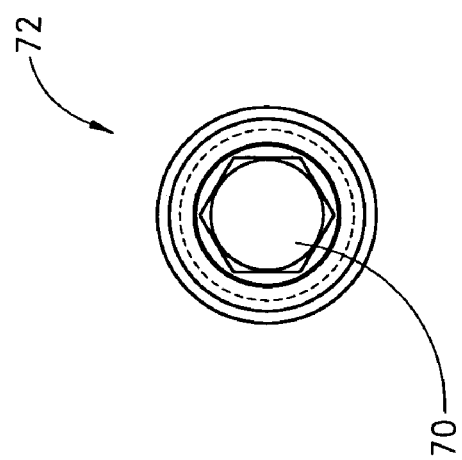
FIG. 3B is a top plan view of the coupling screw of FIG. 3A.
Figure 8D:
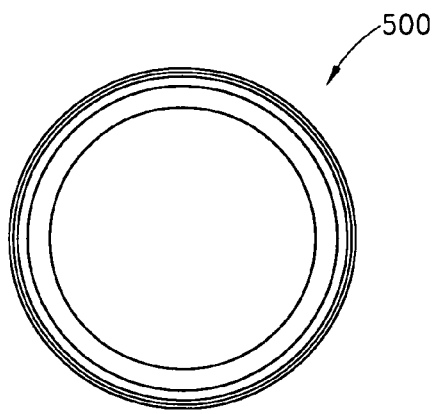
FIG. 8D is a top plan view of the analogue of FIG. 8A.
Figure 8A:
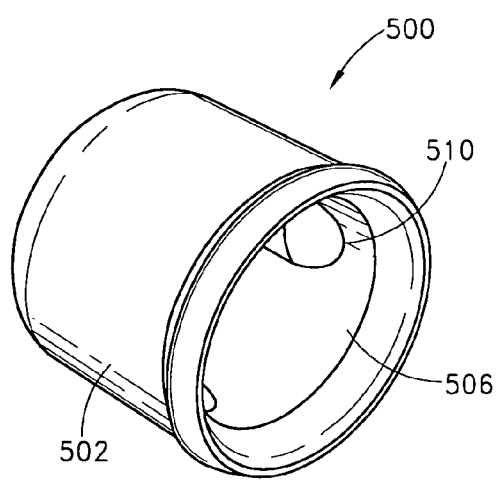
FIG. 8A is side perspective view of a coping.
Figure 8B:
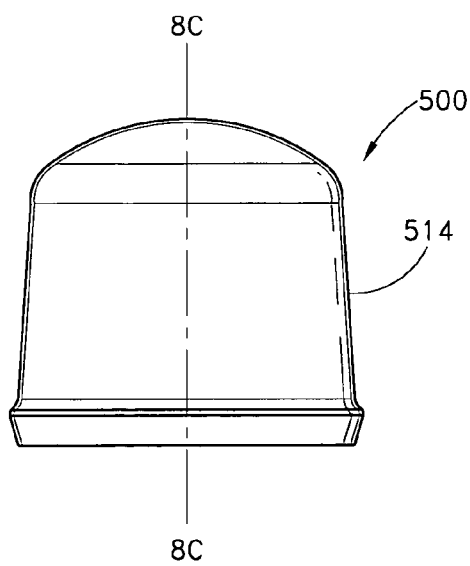
FIG. 8B is a side view of the coping of FIG. 8A.
Figure 8C:
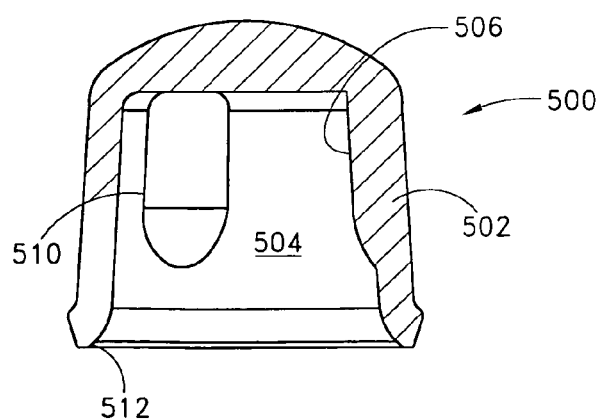
FIG. 8C is a cross-sectional side view taken through line 8C-8C of FIG. 8B.

Turning now to FIGS. 3A and 3B, the coupling screw 62 is sized and dimensioned to extend through the inner bore 52 of the final abutment 38 and to couple the final abutment 38 to the implant 10. As with the final abutment 38, the coupling screw 62 is preferably made of a dental grade titanium alloy. However, other suitable materials can be used.

The coupling screw 62 has an externally threaded lower region 64. The threaded lower region 64 is sized and dimensioned to engage the threads of the threaded chamber 30 of the implant 10 (see FIG. 1C). The threaded lower region 64 can also engage capture threads that can be formed on the second region 56 of the final abutment 38. In such an arrangement, the coupling screw 62 engages the capture threads so that the coupling screw 62 does not become disassociated as the final abutment 38 is transferred and fitted to the patient's mouth.

The illustrated coupling screw 62 also advantageously includes a hexagonal recess 70 located within a head 72 of the screw 62. The hexagonal recess 70 allows for the insertion of a hexagonally shaped tool such as a conventional Allen® wrench, which can be used to apply rotational force to the coupling screw 62. The head 72 also advantageously includes outer threads 74, which are formed on the outer surface 75 of the head 72. The purpose and function of the outer threads 74 will be described below. Alternatively, the threads 74 can be formed internally within the recess 70.

In modified embodiments, the final abutment can be coupled to the dental implant in other manners. For example, the final abutment can include configured a threaded post that is adapted to be received within the threaded chamber 30 of the implant 10. One advantage of such an arrangement is that the final abutment can be attached to the implant without a coupling screw.

FIGS. 4A-4F illustrate one embodiment of a healing cap 76, which can be used to cover the abutment 38 after, for example, stage two surgery. The healing cap 76 may be made of a synthetic polymer, such as, for example, polyester or Nylon. However, it should be appreciated that other suitable materials can also be used. The healing cap 76 is preferably white or close to natural tooth color so that it has a natural appearance when it is placed in the patient's mouth.

The healing cap 76 includes an inner surface 77 which defines an internal cavity 78. The inner surface 77 defines a bottom opening 82. The inner surface 77 is sized and dimensioned such that the healing cap fits over the upper region 40 of the abutment 38. With particular reference to FIG. 4A, the inner surface 77 preferably includes a stop for limiting advance of the healing cap 76 onto the abutment 38, such as, a base surface 84 that is sized and dimensioned to rest against the flanged portion 45 of the final abutment 38. See also FIG. 4C.

Although not illustrated, the healing cap 76 may include a tissue retraction flange that is sized and dimensioned such that when the healing cap 76 is placed upon the abutment 38 it extends beyond at least the upper limit of the shoulder 47 of the final abutment 38.

As best seen in FIGS. 4A, 4D, and 4F, the healing cap 76 preferably has a complementary engagement feature 5 formed within the inner surface 77 and configured to engage the engagement features 3 of the abutment 38 depicted in FIG. 2E. In the illustrated embodiment, the complementary engagement feature 5 comprises a plurality of prongs 7, which include protrusions 9 configured to engage the recess 53 preferably in a snap-fit. In the preferred embodiment, the prongs 7 deflect inwardly as the prongs are advanced into the inner bore 52 and then expand and the protrusions 9 enter the recess 53. Of course, those of skill in the art will recognize other configurations for providing a snap fit between the two components. For example, the cap 76 may include a recess positioned on a post configured to engage a protrusion formed on the bore 52. In addition, as mentioned above, the features 3, 5 can be configured for friction and/or interference fits. Preferably, the features 3, 5 are positioned on the abutment 37 and cap 76 such that they are generally protected from materials within the mouth. In this manner, the features 3, 5 are not damaged as they are inserted within the patient. In the illustrated embodiment, the features 3, 5 are protected by providing an engagement within the bore 52 and/or in a generally upper portion of the cap 76 and abutment 38, distanced from the shoulder 47.

As with the final abutment 38, it should be appreciated that although the illustrated cross-sections of the healing cap 76 are round in modified arrangements the cross-sections can be non-round. For example, the cross-sections can have a non-round cross-section that resembles the cross-section of a natural tooth.

In use, the surgeon typically first places the implant 10 into the patient's jawbone during stage two surgery. A healing cap is placed over the implant. The patient returns home for a first healing period, which is typically four to ten months. In stage three, the surgeon makes an incision to expose the implant 10 and removes the healing cap. The surgeon then couples the final abutment 38 to the implant 10 with the coupling screw 62. The surgeon then places the healing cap 76 over the final abutment 38 and engages the features 3, 5, on the abutment and healing cap respectively, to couple the healing cap 76 to the abutment 38. In the illustrated embodiment, the surgeon presses the healing cap 76 onto the abutment 38 until the features 3, 5 engage in a snap fit. Accordingly, the healing cap 76 is held securely against the final abutment 38. The healing cap 76 helps to control the healing and growth of the patient's gum tissue around the implant site. The healing cap 76 also improves the appearance of the patient's mouth and provides the patient with a temporary chewing surface. If desired, the healing cap 76 can also be used to support a temporary restoration and/or may itself be shaped in the form of a temporary restoration.

The patient then returns home for a second healing period. The patient then returns to the surgeon. The surgeon can pry the healing cap 76 from the abutment 38. At this point, the surgeon takes the impression of the patient's mouth to record the position, orientation and shape of the abutment within the mouth. In a modified arrangement, the abutment 38 can be attached during a traditional stage two surgery. In such an arrangement, an impression of the final abutment 38 can also be made during stage two before the healing cap 76 is attached to the abutment 38. In still a modified arrangement, a temporary abutment preferably having a height at least equal to the thickness of the gingival tissue can be used during the first and/or second healing periods.

In a modified embodiment, the dental implant and abutment can be combined into a single integral or permanently coupled component 200, which is shown in FIGS. 5A-5E. In this embodiment, the abutment 38' and implant 10' can be configured substantially as described above. According, the illustrated embodiment, the implant 10' has an inner bore 52 comprising an upper region 54 and a lower region 56, which is preferably unthreaded. The upper region 54 preferably includes an engagement feature 3, which is a circumferentially extending groove 53 as described above. Additionally, the upper region 54' has one or more anti-rotational features (e.g., longitudinally extending slots 55), which can be engaged by a tool (e.g., a wrench) for driving the implant 200 into the patient. The slots 55 extend between the groove 53 and the threaded lower region 56.

The healing cap 76 can be coupled to the implant 200 as described above.

FIGS. 6A-F illustrate one embodiment of an impression cap 120 having certain features and advantages according to the present invention. As will be explained below, the impression cap 120 can be used to take an impression of an abutment, such as the one described above. In this manner, the shape of the position and/or orientation of the abutment and the implant can be recorded. This information can then be used to construct a final restoration as is known in the art.

The illustrated impression cap 120 comprises a body 122 with a proximal end 124 and a distal end 126. The body 122 is preferably made of resilient moldable plastic and/or polymer, such as, for example, polycarbonate. The body 122 defines an inner surface 128, which forms an inner cavity 130. The inner cavity 130 is configured such that the impression cap 120 can fit over the upper region 40 of the abutment 38. As best seen in FIG. 6C, the inner surface 128 comprises a side wall 134 and roof 136.

The impression cap 120 is preferably configured to engage the abutment 38. Specifically, the impression cap includes a complementary engagement feature 132, which can be configured as describe above for engaging the engagement feature 3 of the implant 10, 200. In the illustrated embodiment, the impression cap 120 engages the implant 10, 200 in a snap fit that is achieved by providing the cap 120 with a plurality of resiliently deflectable prongs 150 with protrusions 152 configured to engage the recess 53 of an abutment, as depicted in FIGS. 2E-F, in a snap fit. Of course, as mentioned above, those of skill in the art will recognize other configurations for providing a snap fit between the two components. For example, the cap 120 may include a recess positioned on a post configured to engage a protrusion formed on the bore 52. In addition, as mentioned above, the features 3, 132 can be configured for friction and/or interference fits. Preferably, the features 3, 132 are positioned on the abutment 37 and cap 120 such that they are generally protected from materials within the mouth and in particular the impression material which is eventually placed around the cap 120. In this manner, the features 3, 150 are not damaged or inhibited.

With reference to FIGS. 6A-C and 6F, the impression cap 120 preferably includes one or more embedment features 160. As will be explained in more detail below, the embedment features 160 facilitate the gripping and retention of the impression cap 120 within an impression tray. The one or more embedment features preferably define at least one interference surface 162, which faces lies generally transverse to a longitudinal axis 164 of the impression cap. In the illustrated embodiment, the embedment feature 160 comprises one or more flanges 166, which are positioned the distal end 126 of the main body 122. In certain embodiments, the flange(s) 166 may include a plurality of through holes 168 (see also FIG. 6B), which extends through the four corners of the flange 166.

A plurality of elongated protrusions 180 are formed on the side wall and sized to engage the grooves 51 of the abutment 38, when the impression cap 120 is positioned thereon. The protrusions 180 and grooves 51 thus mate to substantially prevent the rotation of the impression cap 120 relative to the abutment 38.

The impression cap 120 has angled surfaces 182 at the proximal end 124 that is configured to abut against the flared portion 45 of the implant 10 when the impression cap 120 is positioned thereon.

It should be appreciated that, although the illustrated embodiments of the implant, abutment, healing cap, and impression cap have round cross-sections, in modified arrangements the cross-sections of one or more of these components can be can be non-round.

In use, the impression cap 120 can be used to take an impression of the final abutment 38 and/or record the orientation of the implant 10. Such impression can be taken during stage two or stage three as deemed effective by the dental practitioner. The surgeon snaps the impression cap 120 onto the abutment 38. An impression is then preferably taken of the whole arch or quadrant if the patient's mouth. This typically involves using a U-shaped impression tray (not shown) that is filled with an impression material. The tray is inserted into the mouth over the impression cap 120. As such, the impression cap 120 becomes embedded in the impression material. The interference surface 162 of the cap 120 facilitates mechanically interlocking between the impression material and the impression cap 120. Such interlocking is further enhanced by the holes 168.

Once the impression material is set, the tray 190 is removed from the mouth. The impression cap 120 remains embedded in the impression material 192 and is thus uncoupled from the abutment 38 as the tray 190 is removed. The tray is then sent to a dental laboratory and is used by a dental technician to fabricate a final restoration (i.e., a dental prosthesis). An analogue (described below) of the abutment can be placed within the impression cap, with the same axial orientation as the abutment 38 and the implant 10 in the patient's mouth. The impression tray is then filled or covered with dental stone or any modeling material. After the modeling material has set the model is separated from the impression. The model is an accurate reproduction of the implant site and allows the dental technician to fabricate the final restoration for the patient in the proper position in axial and rotational alignment.

In one embodiment, the abutment, healing cap and/or transfer cap are sold and packaged together as a kit.

FIGS. 7A-7D illustrate an exemplary analogue 400 of the abutment 38 or dental implant 200 described above described above with reference to FIGS. 2A-2F and FIGS. 5A-5E The analogue 400 includes an upper region 402 that has substantially the same shape and size as the upper region 40 of the abutment 38. Accordingly, the upper region 402 of the illustrated analogue 400 also includes a groove or recess 51. The analogue 400 also includes a lower region 404, which is configured to be retained within, by way of example, a stone plaster model of the patient's mouth as is known in the art.

The analogue 400 also includes an inner bore 406 with an engagement feature 3, which can be configured as described above to engage complementary engagement figure of another component. In particular, as mentioned above, the analog can be inserted into the impression cap 120 so as to take the same axial orientation as the abutment 38 and the implant 10 in the patient's mouth. The impression tray is then filled or covered with dental stone or any modeling material. The lower region 404 of the analogue 400 is embedded into the modeling material. After the modeling material has set the model is separated from the impression. The model is an accurate reproduction of the implant site and allows the dental technician to fabricate the final restoration for the patient in the proper position in axial and rotational alignment.

FIGS. 8A-D illustrate a coping 500 that can be used to fabricate the final restoration. The illustrated coping 500 is configured to mate with the exemplary abutment 38 (or implant 300) and analogue 400 described above. Of course, those skilled in the art will recognize that the illustrated coping can be modified to mate with abutments and analogues of different shapes and sizes.

The coping 500 comprises a main body 502. The main body 502 includes an inner surface 506 that defines an internal cavity 504. The inner surface 506 is configured such that the coping 500 can fit over the upper region 402 of the analogue 400 and the final abutment 38 described above. Accordingly, the coping 500 includes at least one anti-rotation member 510, which is configured to mate with the recess 51 of the analogue and recess of the abutment so as to prevent rotation of the coping 500 with respect to the analogue 400 and/or the abutment 38.

The inner surface can include includes one or more feet or standoffs (not shown). See e.g., U.S. Pat. No. 6,672,871, the entire contents of which are hereby incorporated by reference herein.

The inner surface 506 also preferably includes a flanged portion 512. The flanged portion 512 is configured to rest upon a lower portion or shoulder of the analogue 400 and the abutment 38. Preferably, the flanged portion is sized and configured such that the coping is centered on the analogue.

In one embodiment, the coping 500 is used with investment casting techniques to create a metal coping with an inner surface substantially similar to the inner surface 506 of the coping 500. In this method, the coping 500 is preferably made of plastic or another material suitable for investment casting. The technician applies, by way of example, wax to the outer surface 514 of the coping 500 to form a model of a metal coping. The technician removes the wax and the coping 500 from the analogue 400 and encases the combination in an investment material. The investment material is then heated to remove the wax and coping 500. The technician fills the investment material with a metal, such as, for example, gold or another suitable material. Once the metal solidifies, the investment material is broken to release the metal coping. To form the final restoration, a porcelain cover or other suitable tooth-like material is attached to the metal coping using well known techniques. The metal coping provides structural strength and rigidity to the final restoration. The final restoration can be coupled to the abutment 38 or implant 300 using cement, bolts or other well-known techniques.

In a modified embodiment, the coping 500 is made of material suitable for forming part of a final restoration, such as, for example, gold or a ceramic material. Preferably, the material is a ceramic fusing metal material to which, by way of example, porcelain can be directly fused. The coping 500 has substantially the same shape and size as the plastic coping described above. Because the coping 500 is made of a fairly rugged material, the coping can form part of the final restoration. That is, a cover made of porcelain or other suitable material can be directly attached to the coping 500, thereby forming the final restoration.

In one embodiment, the abutment, healing cap, coping, analogue and/or transfer cap are sold and packaged together as a kit.

Although invention has been disclosed in the context of certain preferred embodiments and examples, it will be understood by those skilled in the art that the present invention extends beyond the specifically disclosed embodiments to combinations, sub-combinations, other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A dental implant component, the component comprising:
   a distal end that includes a top surface;
   a proximal end that defines an opening;
   an inner surface that defines an internal cavity that is substantially closed at the distal end of the component; and
   at least one resiliently deflectable prong disposed in the internal cavity, the prong configured to releasingly engage one or more grooves formed in a bore of a prosthetic abutment, the inner surface extending longitudinally beyond the prong;
   a proximally facing slanted surface at the proximal end configured to abut against a flared flange of the abutment;
   one or more embedment features for facilitating the gripping and retention of the component within impression material and positioned on the distal end of the component;
   wherein the one or more embedment features comprises a flange, which defines an interference surface that lies generally transverse to a longitudinal axis of the component.

2. A dental implant component as in claim 1, wherein the prong is configured to engage the one or more grooves of the abutment in a snap fit.

3. A dental implant component as in claim 1, wherein the prong includes a protrusion formed on an outer surface of the prong, the protrusion sized and dimensioned so as to engage the corresponding groove of the prosthetic abutment in a snap fit.

4. A dental implant component as in claim 1, wherein the flange is positioned at the distal end of the component.

5. A dental implant component as in claim 1, wherein the flange includes one or more through-holes.

6. A dental implant component as in claim 1, wherein the inner surface of the component comprises a top surface that generally faces the proximal end of the component and wherein the prong extends proximally from the top surface.

7. A dental implant system, the system comprising:
   a dental implant;
   an abutment comprising an upper region and an inner bore having at least one engagement feature positioned therein;
   a mating component having a distal end that includes a top surface, a proximal end that defines an opening, an inner surface that defines an internal cavity that is substantially closed at the distal end of component for receiving the upper region of the abutment, at least one complementary engagement feature disposed in the internal cavity and configured to releaseably engage the engagement feature within the inner bore, the inner surface extending longitudinally in a proximal direction beyond the complementary engagement feature, and at least one anti-rotational feature formed on the inner surface of the mating component for engaging at least one complementary anti-rotational feature formed on the abutment to substantially prevent rotation of the mating component relative to the abutment in an assembled configuration;

wherein the engagement feature and complementary engagement feature are configured to provide a snap-fit;

one or more embedment features for facilitating the gripping and retention of the component within impression material and positioned on the distal end of the component;

wherein the one or more embedment features comprises a flange, which defines an interference surface that lies generally transverse to a longitudinal axis of the component.

8. The dental system as in claim 7, wherein the engagement feature and complementary engagement feature are configured to provide an interference fit.

9. The dental system as in claim 7, wherein the mating component is a transfer cap with features for engaging impression material.

10. The dental system as in claim 7, wherein the abutment is coupled to the implant by a screw.

11. The dental system as in claim 7, wherein the abutment is integrally formed with the dental implant.

12. The dental component as in claim 7, wherein the at least one anti-rotational feature comprises an elongate protrusion and the at least one complementary anti-rotational feature comprises an elongate groove.

* * * * *

UNITED STATES PATENT AND TRADEMARK OFFICE
CERTIFICATE OF CORRECTION

| | | |
|---|---|---|
| PATENT NO. | : 8,272,871 B2 | Page 1 of 1 |
| APPLICATION NO. | : 11/377259 | |
| DATED | : September 25, 2012 | |
| INVENTOR(S) | : Hurson | |

It is certified that error appears in the above-identified patent and that said Letters Patent is hereby corrected as shown below:

Title Page (item 73, Assignee) at line 1, Change "Service" to --Services--.

In the Specifications
In column 1 at line 13, Change "herein" to --herein.--.
In column 8 at line 31, Change "3,5" to --3, 5--.

In the Claims
In column 14 at line 3, In Claim 8, after "dental" insert --implant--.
In column 14 at line 6, In Claim 9, after "dental" insert --implant--.
In column 14 at line 9, In Claim 10, after "dental" insert --implant--.
In column 14 at line 11, In Claim 11, after "dental" insert --implant--.
In column 14 at line 13, In Claim 12, delete "component" and insert --implant system--.

Signed and Sealed this
Fifteenth Day of April, 2014

Michelle K. Lee
*Deputy Director of the United States Patent and Trademark Office*